United States Patent [19]

Mehra

[11] Patent Number: 5,243,980
[45] Date of Patent: Sep. 14, 1993

[54] METHOD AND APPARATUS FOR DISCRIMINATION OF VENTRICULAR AND SUPRAVENTRICULAR TACHYCARDIA

[75] Inventor: Rahul Mehra, Stillwater, Minn.

[73] Assignee: Medtronic, Inc., Minneapolis, Minn.

[21] Appl. No.: 906,806

[22] Filed: Jun. 30, 1992

[51] Int. Cl.$^5$ .............................................. A61N 1/00
[52] U.S. Cl. ........................................ 607/6; 128/705; 128/697; 128/703
[58] Field of Search ........ 128/419 PG, 419 D, 419 P, 128/419 PT, 419 S, 786, 697, 703, 704, 705

[56] References Cited

U.S. PATENT DOCUMENTS

| | | | |
|---|---|---|---|
| 3,737,579 | 6/1973 | Bolduc | 128/418 |
| 4,313,448 | 2/1982 | Stokes | 128/785 |
| 4,375,817 | 3/1983 | Engle et al. | 128/419 |
| 4,384,585 | 5/1983 | Zipes | 128/419 |
| 4,402,330 | 9/1983 | Lindemans | 128/786 |
| 4,548,209 | 10/1985 | Wielders et al. | 128/419 |
| 4,577,633 | 3/1986 | Berkovits et al. | 128/419 |
| 4,587,970 | 5/1986 | Holley et al. | 128/419 |
| 4,693,253 | 9/1987 | Adams | 128/419 |
| 4,726,380 | 2/1988 | Vollmann et al. | 128/419 |
| 4,727,877 | 3/1988 | Kallok | 128/419 |
| 4,800,883 | 1/1989 | Winstrom | 128/419 |
| 4,817,634 | 4/1989 | Holleman et al. | 128/784 |
| 4,830,006 | 5/1989 | Haluska et al. | 128/419 |
| 4,880,005 | 11/1989 | Pless et al. | 128/419 |
| 4,949,719 | 8/1990 | Pless et al. | 128/419 |
| 4,949,730 | 8/1990 | Cobben et al. | 128/775 |
| 4,953,551 | 9/1990 | Mehra et al. | 128/419 |
| 5,014,696 | 5/1991 | Mehra | 128/419 |
| 5,044,374 | 9/1991 | Lindemans et al. | 128/784 |
| 5,107,850 | 4/1992 | Olive | 128/419 D |
| 5,117,824 | 6/1992 | Keimel et al. | 128/419 |
| 5,144,960 | 9/1992 | Mehra et al. | 128/786 |
| 5,161,527 | 11/1992 | Nappholz et al. | 128/419 PG |

OTHER PUBLICATIONS

Attorney's Dictionary of Medicine and Word Finder, by J. E. Schmidt, M.D., Matthew Bender, 235 E. 45th Street, New York, N.Y., 10017, p. F-11.

Cooper et al., "Neural Effects on Sinus Rate and Atrioventricular Conduction Produced by Electrical Stimulation from a Transvenous Electrode Catheter in the Canine Right Pulmonary Artery", Circulation Research, vol. 46, No. 1, Jan. 1980, pp. 48-57.

Jenkins et al., "A Single Atrial Extrastimulus Can Distinguish Sinus Tachycardia from 1:1 Proxysmal Tachycardia", Pace, vol. 9, Nov.-Dec. 1986, Part II, pp. 1063-1068.

Olson et al., "Onset and Stability for Ventricular Tachyarrhythmia Detection in an Implantable Pacer-Cardioverter-Defibrillator", Computer in Cardiology, Oct. 7-10, 1986, pp. 167-170.

Randall et al., "Functional Anatomy of the Cardiac Efferent Innervation", Neurocardiology, Mount Kisco, N.Y., Futura Publishing Co., Inc. 1988, pp. 3-24.

Thacker et al., "Reliable R-Wave Detection from Ambulatory Subjects", Biomedical Science Instrumentation, vol. 4, pp. 67-72, 1978.

*Primary Examiner*—William E. Kamm
*Assistant Examiner*—George Manuel
*Attorney, Agent, or Firm*—Reed A. Duthler; Harold R. Patton

[57] ABSTRACT

A method for discrimination between ventricular and supraventricular tachycardia and an apparatus for performing the method. In response to the detection of the occurrence of an tachycardia, stimulus pulses are delivered to one or both of the SA and AV nodal fat pads. The response of the heart rhythm to these stimulus pulses is monitored. Depending upon the change or lack of change in the heart rhythm, a diagnosis is made as to the origin of the tachycardia.

44 Claims, 11 Drawing Sheets

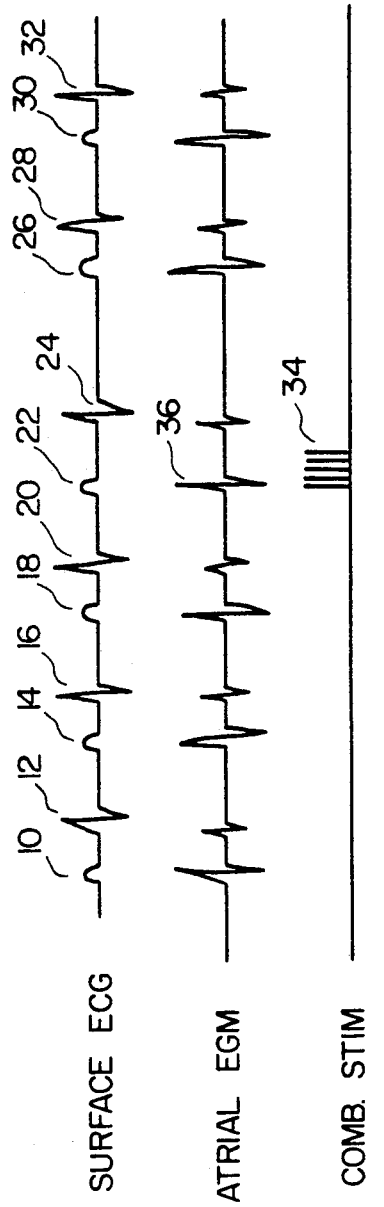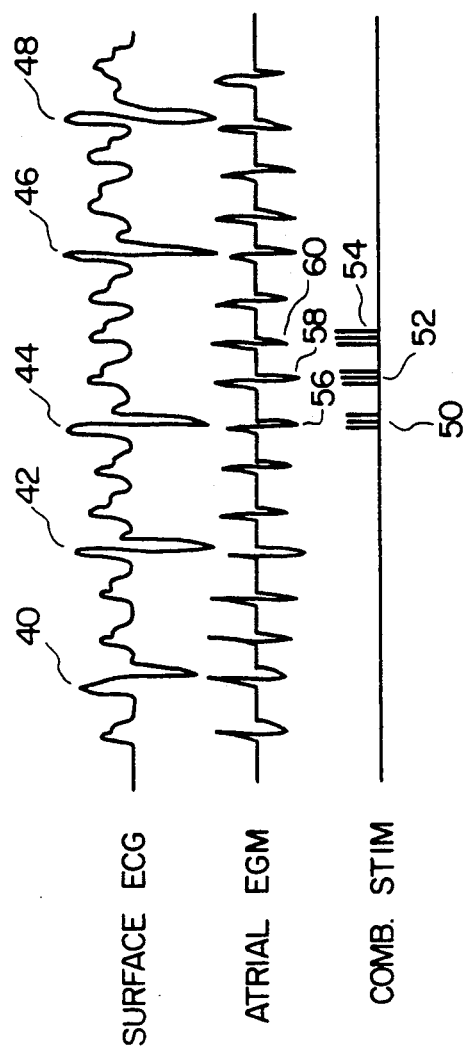

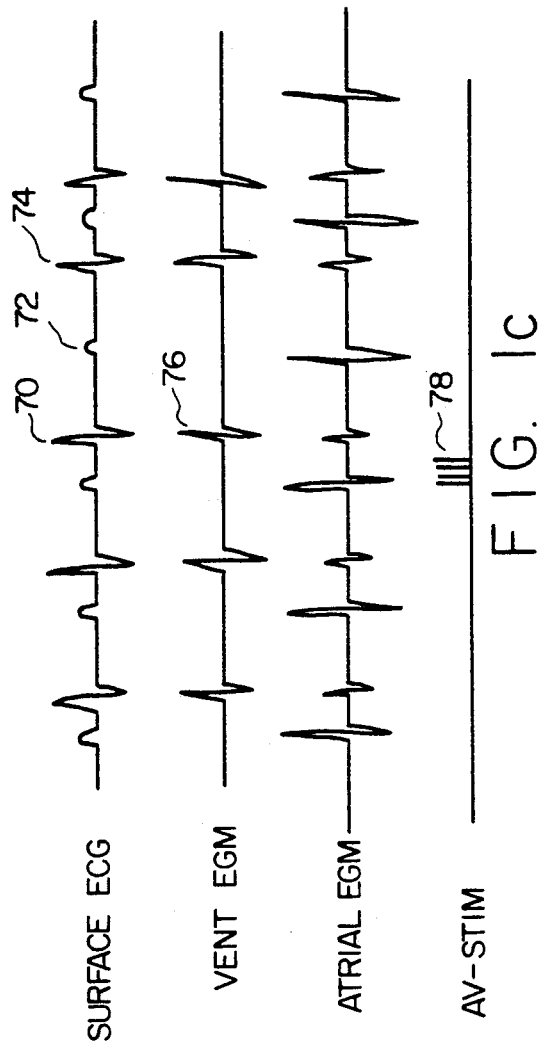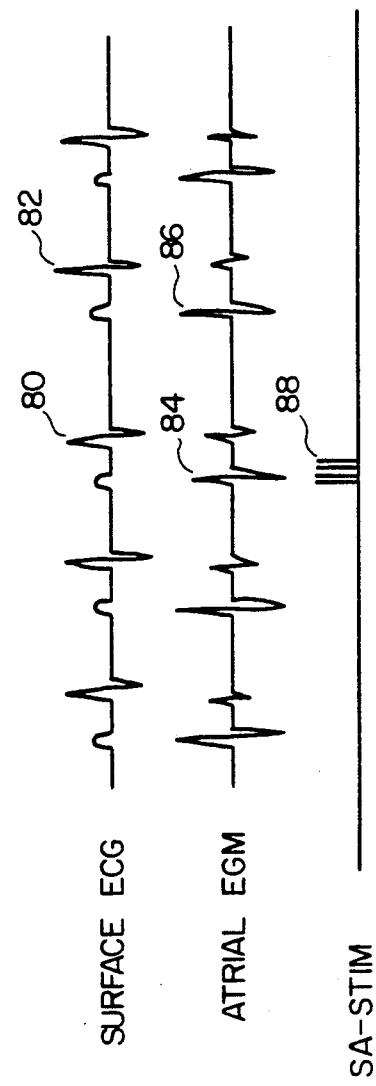

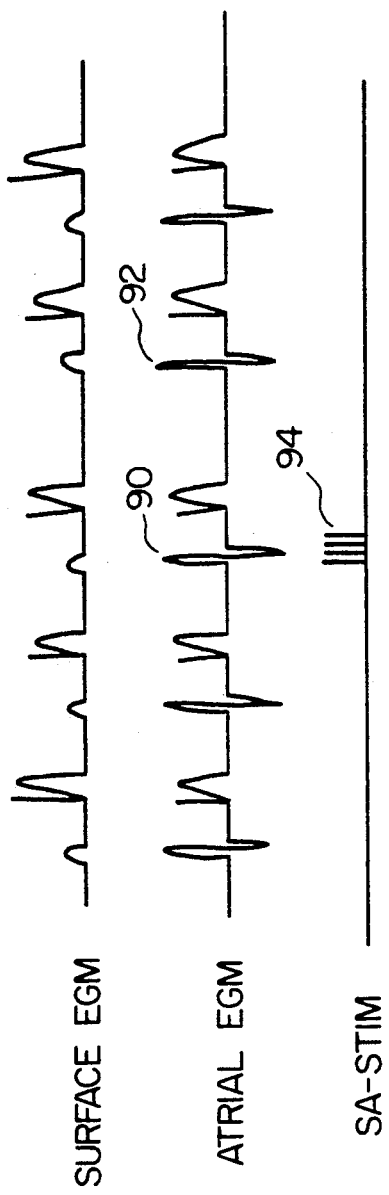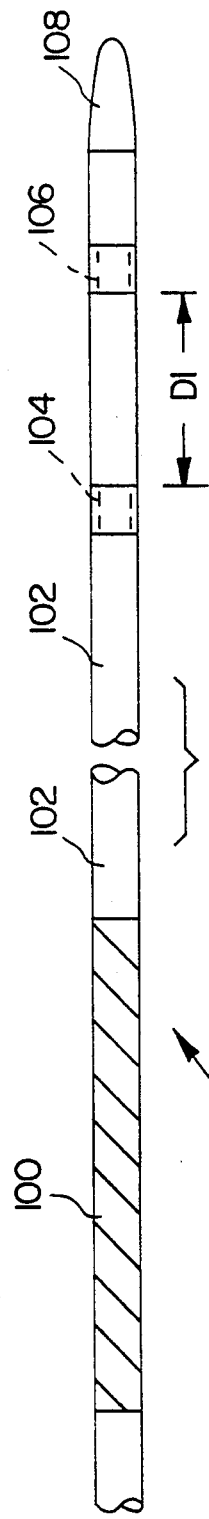

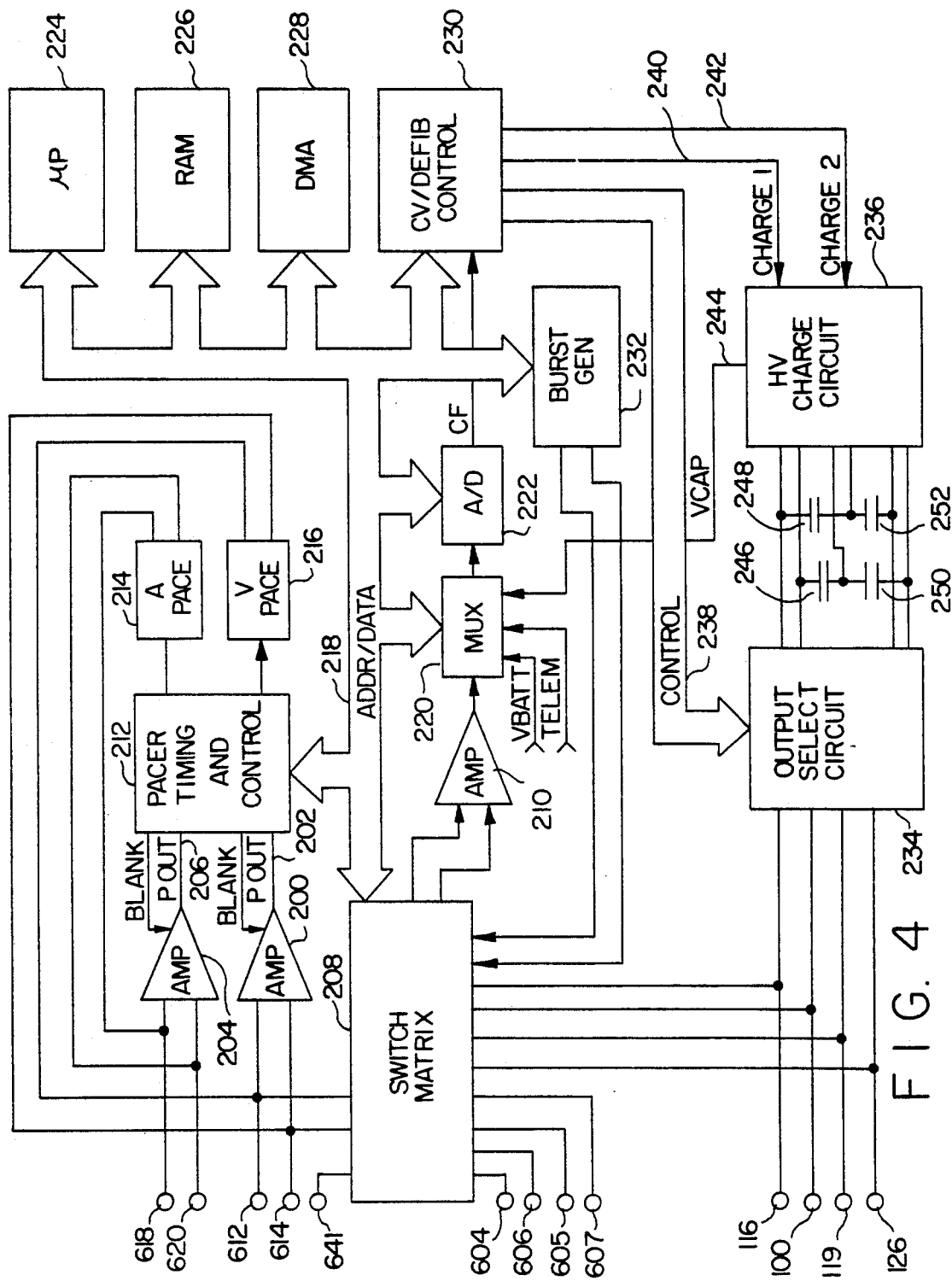
F I G. 4

METHOD AND APPARATUS FOR DISCRIMINATION OF VENTRICULAR AND SUPRAVENTRICULAR TACHYCARDIA

BACKGROUND OF THE INVENTION

This invention relates to implantable stimulators generally and more particularly to implantable cardioverters and defibrillators.

Automatic tachycardia detection systems for previously disclosed automatic cardioverter/defibrillators presently have relied upon the presence or absence of electrical and mechanical heart activity (such as intramyocardial pressure, blood pressure, impedance, stroke volume or heart movement) and/or the rate of the electrocardiogram to detect hemodynamically compromising ventricular tachycardia or fibrillation. Others have suggested the use of physiological sensors such as oxygen saturation sensors to diagnose various types of tachyarrhythmias.

Very generally, the systems that depend upon the aforementioned criteria are capable of discriminating tachycardia in greater or lesser degree from normal heart rate but can have difficulty discriminating ventricular tachycardias from supraventricular tachycardias or in distinguishing sinus tachycardias from non-sinus tachycardias in some circumstances which may result in delivery of inappropriate antitachycardia therapies.

Use of pacing stimuli to discriminate between types of tachyarrhythmias has also been proposed. In the article, "A Single Atrial Extrastimulus Can Distinguish Sinus Tachycardia from 1:1 Paroxysmal Tachycardia" by Jenkins et al, published in Pace, Vol. 9, Part II, Nov.-Dec., 1986, delivery of an atrial premature stimulus is disclosed as a method of distinguishing sinus tachycardia from ventricular tachycardia with one to one retrograde conduction or A-V nodal reentrant tachycardia. This article also discusses various methods of distinguishing among types of tachycardias based upon timing of spontaneous atrial and ventricular contractions.

It is known that stimulation of the vagus nerves can vary the heart's rhythm. This phenomena has often been proposed as a method of treating tachyarrhythmias. It is also known that the nervous system regulating the rhythm of the heart includes a number of highly ganglionated plexi or "fat pads" at various locations on the heart, including fat pads associated with the SA and AV nodes. As set forth in "Functional Anatomy of the Cardiac Efferent Innervation", by Randall et al, in *Neurocardiology*, edited by Kulbertus et al, Futura Publishing Co., 1988, direct epicardial stimulation of the fat pad associated with the SA node can produce a slowing of the sinus rate and stimulation of the fat pad associated with the AV node can result in a prolongation of the P-R interval or production of A-V block. The effects of stimulation of individual ones of the fat pads are limited to their associated nodes.

As set forth in the article "Neural Effects on Sinus Rate and Atrial Ventricular Conduction Produced by Electrical Stimulation From a Transvenous Electrode Catheter in the Canine Right Pulmonary Artery" by Cooper et al., published in Circulation Research, Vol. 46, No. 1, Jan., 1980, pp. 48-57, the fat pads associated with both the AV node and the sinus node may be stimulated by means of electrodes located in the right pulmonary artery. The results obtained include both a depression of the sinus rate and a prolongation of the A-V conduction time in response to continuous stimulation at 2-80 Hz at up 50 ma.

SUMMARY OF THE INVENTION

In the context of an automatic implantable device for treating bradyarrhythmias, tachyarrhythmias and fibrillation, the present invention comprises a method and apparatus for reliable discrimination of ventricular tachycardias from supraventricular tachycardias and for specifically identifying sinus tachycardias.

The inventor of the present invention has determined that this physiological phenomena discussed in the above-cited Cooper and Randall articles provides an opportunity in the context of an implantable arrhythmia treatment device for accurately distinguishing between ventricular and supra ventricular tachyarrhythmias.

The inventor of the present application has further determined that continuous stimulation of the sort set forth in the Cooper et al. article often leads to induction of atrial fibrillation. However, the inventor has determined that by providing only limited bursts of stimulation, synchronized to detected atrial contractions, the problem of atrial fibrillation induction can be avoided. Moveover, the desired results of slowing the sinus rate, and/or extending the P-R interval can still be accomplished. These factors allow the use of electrical stimulation of the AV and SA nodal fat pads to be used to provide a method of discrimination between ventricular and supraventricular tachycardias.

As set forth in the more detailed description below, it is believed that the method of discrimination between ventricular tachycardias and supraventricular tachycardias and for identification of sinus tachycardias provided by the present invention will optimally be embodied in a device which includes electrodes for sensing both atrial and ventricular depolarizations. After detection of a high ventricular rate indicative of tachycardia, the present invention may be employed by stimulating the AV nodal and/or SA nodal fat pads synchronized to detected atrial and/or ventricular depolarizations. Stimulation may be accomplished by means of catheters carrying electrodes located in the right pulmonary artery, right atrium and/or coronary sinus. Stimulation may instead be accomplished by means of epicardial or myocardial electrodes applied to the fat pads. Alternatively, combined stimulation of the AV and SA nodal fat pads may be accomplished by means of vagal nerve stimulation using nerve bundle electrodes, however this is not believed to be the optimal approach to practicing the present invention.

If the tachyarrhythmia is ventricular in origin, stimulation of either of the SA nodal or AV nodal fat pad will not result in a change in ventricular rate. If the tachyarrhythmia is supraventricular in origin, or is a sinus tachycardia, the result of fat pad stimulation will be a reduction in the atrial rate, and/or an extension of the P-R interval, and a corresponding reduction in the ventricular rate, depending on which fat pad or pads are stimulated. These induced changes in cardiac rhythm are detected and are used in the present invention to identify the origin of the detected tachyarrhythmia.

The present invention, by providing a mechanism for more accurately discriminating among the various types of tachyarrhythmias provides the opportunity to treat detected tachyarrhythmias properly and promptly. The present invention may also be combined with and used in conjunction with tachycardia detection and discrimination algorithms of the type discussed in the background of the invention. Interrelation of the discrimination function provided by the present invention with such prior art tachyarrhythmia detection and discrimination methodologies is discussed in more detail below.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which:

FIGS. 1a, 1b, 1c, 1d and 1e are simulated ECG and EGM tracings, illustrating the basic operation of the present invention.

FIG. 2 is an illustration of the distal end of one embodiment of a combination defibrillation and fat pad stimulation lead adapted for use in conjunction with the present invention.

FIG. 4 is a functional block diagram illustrating an implantable pacemaker/cardioverter/defibrillator in which the present invention may be embodied.

DETAILED DESCRIPTION OF THE PREFERRED EMBODIMENTS

Figure 3A:
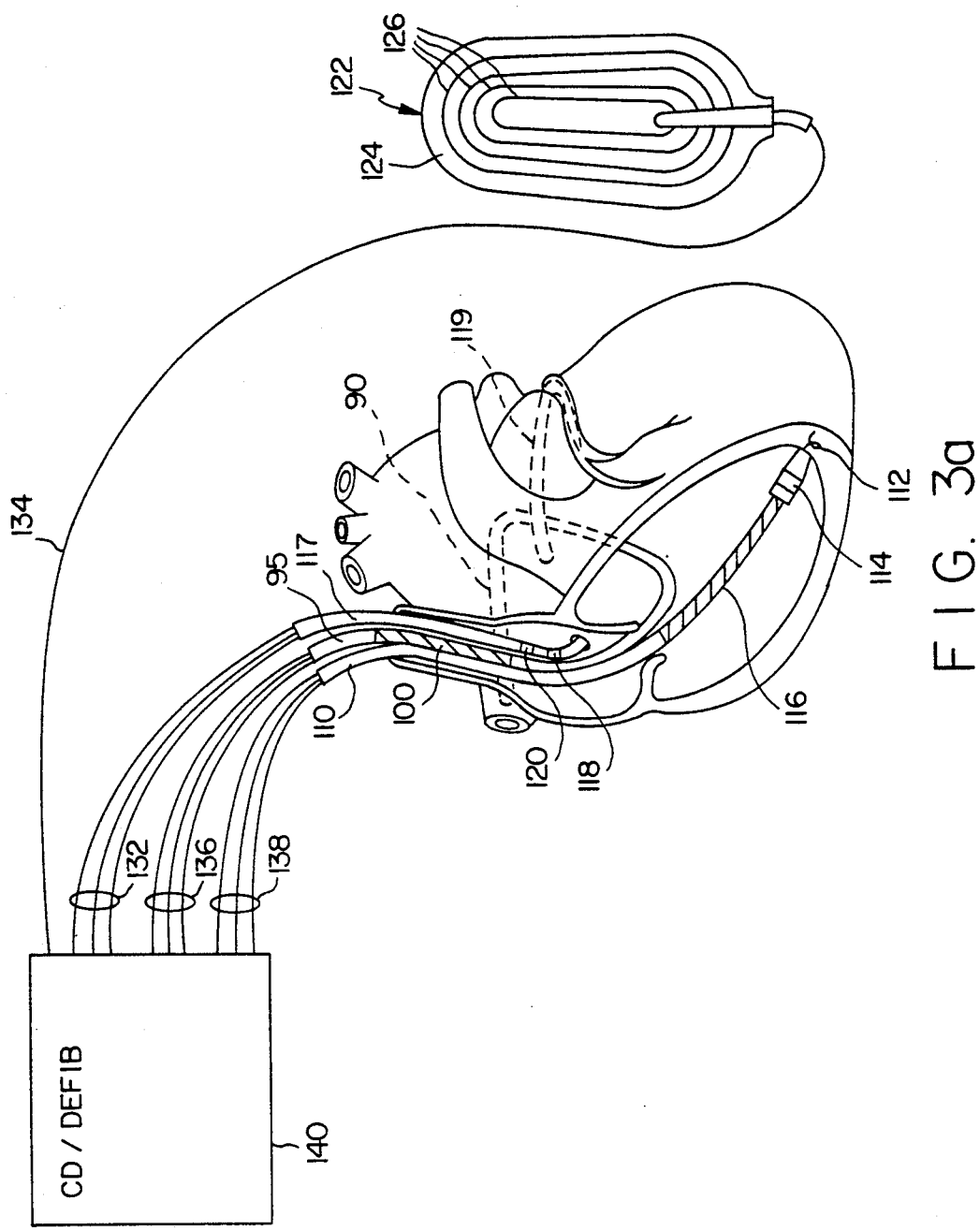
FIGS. 3a and 3b are illustrations of the heart and of various lead systems for use with the present invention.

FIG. 1a illustrates a method of tachycardia discrimination performed employing the present invention. As illustrated in the simulated surface ECG strip, a high atrial rate is present as manifested by P-waves, 10, 14, 18, 22. For each P-wave there is a corresponding R-wave, 12, 16, 20, 24, indicative of a ventricular depolarization. The simulated atrial EGM shows corresponding P-waves and R-waves. From an examination of the surface ECG or of the atrial EGM, it is not clear whether the rapid rhythm is due to an A-V nodal reentry tachycardia, sinus tachycardia or ventricular tachycardia with one to one retrograde conduction. The device embodying the invention delivers one or more bursts of stimuli, each burst comprising several individual pulses. In the illustrated case, the pulses are delivered to both the AV and SA nodal fat pads at 34, synchronized with the detection of the atrial depolarization at 36, sensed from the atrial EGM. The result is an extension in the interval separating the atrial depolarization 36 from the subsequent ventricular depolarization 24. This reflects a prolongation of the P-R interval due to stimulation of the AV nodal fat pad. In addition, the sinus rate is decreased, as indicated by an increase in the interval between atrial depolarizations 22 and 26 and a corresponding increase in the interval between ventricular depolarizations 24 and 28.

After delivery of the stimulation pulses, the heart rhythm quickly returns to its previous condition, as illustrated by atrial depolarizations 26 and 30 and by ventricular depolarizations 28 and 32. The increase in the P-R interval and the increase in the R-R interval both indicate that the tachycardia is supraventricular in origin. The increase in the P-P interval indicates that the patient is undergoing sinus tachycardia, which typically cannot be treated by means of electrical stimulation. An increase of the P-R and R-R intervals, without a corresponding increase in the P-P interval would indicate that the source of the arrhythmia is supraventricular, but non-sinus. No change at all in the R-R interval would indicate that the tachycardia is ventricular in origin. With this information, the accuracy of selection of an electrical therapy appropriate to terminate the tachycardia is increased.

FIG. 1b illustrates the operation of the invention in the case in which simultaneous high atrial and ventricular rates are detected, and the atrial rate is in excess of the ventricular rate. In the case illustrated, the high ventricular rate is due to atrial tachycardia or flutter, leading to intermittent conduction to cause generation of ventricular depolarizations 40, 42, 44, 46 and 48. In response to detection of a high rate in the ventricle, the device is configured to provide pulse bursts synchronized with atrial depolarizations sensed using the atrial EGM until either a ventricular contraction is sensed or until a maximum number of bursts (e.g. 3) has been delivered. The device thus delivers pulse bursts 50, 52 and 54 to stimulate both the AV and SA nodal fat pads, each burst synchronized to one of atrial depolarizations 56, 58 and 60.

In this case, the result of the stimulation pulses is either to temporarily decrease the number of atrial depolarizations which are propagated through the AV node or to increase the A-V conduction time, leading to a decrease in sensed ventricular rate for at least one R-R interval, as indicated by the wider spacing between ventricular depolarization 44 and ventricular depolarization 46. This result indicates that the tachycardia is of supraventricular origin. The invariant atrial rhythm in conjunction with the variation in ventricular rate indicates that the high atrial rate is not of sinus origin. After cessation of stimulation, the heart returns to its previous rhythm as indicated by ventricular depolarizations 46 and 48.

If no change in the ventricular rhythm had resulted, a tachycardia of ventricular origin in conjunction with concurrent atrial tachycardia, flutter or fibrillation not conducted 1:1 to the ventricles would be-indicated. Thus, in the circumstances in which the atrium and ventricle both display high rates, with the atrial rate being the higher of the two, the present invention can also facilitate selection of an appropriate therapy.

As an alternative, in the situation illustrated in FIG. 1b, a device provided with electrodes capable of individually stimulating the AV nodal fat pad only may also be employed, delivering a pulse burst synchronized to a detected ventricular depolarization. Prolongation of the R-R interval would similarly indicate a supraventricular origin of the tachyarrhythmia.

FIG. 1c illustrates the operation of the invention in an embodiment employing electrodes adapted to individually stimulate the AV nodal fat pad. As illustrated by the simulated surface ECG, simultaneous high atrial and ventricular rates are present with 1:1 correspondence between atrial and ventricular contractions. The device embodying the invention delivers a train of stimulus pulses 78 synchronized to the sensed ventricular contraction 76 sensed from the ventricular EGM.

The result is an extension of the R-R interval separating ventricular depolarization 70 from the next subsequent ventricular depolarization 74 and a prolongation of the P-R interval separating atrial depolarization 72 from ventricular depolarization 74, indicating a supraventricular origin for the tachycardia. In this case, subsequent stimulation of the SA nodal fat pad as discussed in conjunction with FIG. 1d, below would distinguish whether the tachycardia is sinus or non-sinus in origin. Had the R-R interval remained invariant, a ventricular tachycardia would be indicated.

FIG. 1d illustrates the operation of the invention in an embodiment employing electrodes adapted to individually stimulate the SA nodal fat pad. As illustrated by the simulated surface ECG, Simultaneous high atrial and ventricular rhythms are present with one to one correspondence between atrial and ventricular depolarizations. The device embodying the invention delivers a train of pulses 88 synchronized to atrial depolarization 84, sensed from the atrial EGM.

As a result, the P-P interval separating atrial depolarizations 84 and 86 is increased, along with the R-R interval separating ventricular depolarizations 80 and 82, indicating that a sinus tachycardia is present. Had there been no change in R-R and P-P intervals, a non-sinus tachycardia would be indicated. In this case, subsequent stimulation of the AV nodal fat pad as in FIG. 1c would distinguish whether the tachycardia is ventricular or supraventricular in origin.

FIG. 1e illustrates yet another situation in which the present invention may be usefully practiced. In this case, it is assumed that the patient has undergone AV nodal ablation and is provided with an atrial synchronous (VDD, DDD, VDDR or DDDR) pacemaker. In this case, determining whether high atrial rates are sinus or non-sinus is still of value, particularly to distinguish high sinus rates indicative of exercise, which should result in synchronized ventricular pacing, from atrial tachycardias or flutter, which should not result in corresponding ventricular pacing. This aspect of the invention is similarly valuable in conjunction with an implanted atrial cardioverter, allowing for discrimination between sinus tachycardias which will not be treated and atrial flutter or tachycardias, which may be treated.

As illustrated, a high atrial rate is present, with ventricular pacing following the sensed atrial depolarizations. Stimulation of the SA nodal fat pad occurs at 94, synchronized to atrial depolarization 90, sensed from the atrial EGM. The resulting prolongation of the P-P interval separating atrial depolarizations 90 and 92, indicates that a sinus rhythm is present. Ventricular pacing synchronized to the sensed atrial depolarizations thus continues. If no change in atrial rhythm occurred, a change in pacing mode from atrial synchronous to non-synchronous (VVI, DDI) might be triggered. In the context of an atrial cardioverter assuming the atrial rate is indicative of tachycardia, the diagnosis of sinus tachycardia would result in no cardioversion therapy being delivered. If no change in atrial rhythm occurred, cardioversion or antitachycardia pacing therapies would be delivered.

FIG. 2 is a plan view of the distal portion of a combined defibrillation and fat pad stimulation lead 95. The lead is provided with an elongated defibrillation electrode 100, mounted to an insulative, elongated lead body 102. This electrode 11 is intended to be placed in the superior vena cava or other location within the heart. At the distal end of the lead are two electrodes 104 and 106, used for fat pad stimulation, and intended to be located in the right pulmonary artery, adjacent the right atrium. An appropriate spacing D for these electrodes may be 5 to 10 centimeters. However, experimentation by the inventor has led to the determination that precise location is not required, so long as the electrodes 104 and 106 are located posterior to the right atrium. At the distal end of the lead is an insulative, flexible tip 108, to assist passage of the lead through the vascular system. Defibrillation electrode 100 and electrodes 104 and 106 may all be made using conventional electrode construction techniques well known to the art, and are each coupled to an individual insulated conductor within lead body 102, allowing the electrodes to be coupled to a pacemaker/cardioverter/defibrillator.

FIG. 3a is a cutaway view of the heart illustrating an implantable cardioverter/defibrillator and associated lead system. A ventricular defibrillation lead 11 carries a bipolar electrode pair located at the right ventricular apex. The electrode pair includes a tip electrode 112, which takes the form of a helical electrode screwed into the right ventricular myocardium and a ring electrode 114. The lead also includes an elongated coiled defibrillation electrode 116. The illustrated lead corresponds generally to the leads described in U.S. Pat. No. 5,014,696, issued May 14, 1991 to Mehra for an Endocardial Defibrillation Electrode System, incorporated herein by reference in its entirety. Each of the electrodes 112, 114, and 116 is coupled to one of three mutually insulated conductors 138, Which conneCt them to an implanted pacemaker/cardioverter/defibrillator 140.

The lead system also comprises a pulmonary artery lead 95, corresponding to the lead illustrated in FIG. 2. The pulmonary artery lead 95 is provided with an elongated defibrillation electrode 100 located in the superior vena cava and a pair of electrodes 104, 106, (FIG. 2) not visible in this view located adjacent and posterior to the right atrium at the distal end of lead 90. Each of the electrodes 100, 104, 106 is coupled to one of three mutually insulated conductors 136 which connect them to defibrillator 140.

Alternatively, the pulmonary artery electrodes could be carried on a bifurcated ventricular defibrillation lead corresponding generally to the lead described in copending allowed U.S. Pat. Application Ser. No. 07/672,285 by Mehra et al for a "Transvenous Defibrillation Lead, filed Mar. 30, 1999 and incorporated herein by reference in its entirety, with an extension of the portion of the lead lying in the ventricular outflow tract carrying two electrodes corresponding to electrodes 104 and 106 (FIG. 2), located posterior to the right atrium.

A coronary sinus lead 117 is provided carrying an elongated defibrillation electrode 119, illustrated in broken outline, located within the coronary sinus and great vein and extending around the heart to approximately the point at which the great vein turns downward toward the apex of the heart. The lead 117 is also provided with two ring electrodes 118 and 120 located within the atrium and intended for use in sensing and stimulating the atrium. Electrodes 118, 119 and 120 are each coupled to one of three mutually insulated conductors 132 which couple them to implanted pacemaker/cardioverter/defibrillator 140. Lead 117 may correspond to the coronary sinus/great vein lead disclosed in the above cited U.S. Pat. No. 5,014,696 by Mehra.

Subcutaneous lead 122 is implanted in the left chest and includes a large surface electrode pad 124, carrying four elongated electrode coils 126, all coupled to insulated conductor 134, which connects them to defibrillator 140. Electrode 122 may correspond to the electrode illustrated in allowed U.S. Pat. Application Ser. No. 07/376,730, by Lindemans et al. for a Medical Electrical Lead, filed Jul. 7, 1989 and incorporated herein by reference in its entirety.

Other defibrillation leads may also be employed, such as epicardial leads as disclosed in U.S. Pat. No. 4,817,634, issued to Holleman et al on Apr. 4, 1989 and incorporated herein by reference in its entirety. Similarly in some embodiments, provision of endocardial atrial sensing and pacing electrodes located on a separate lead, such as disclosed in U.S. Pat. No. 4,402,330, issued to Lindemanns on Sep. 6, 1983 and incorporated herein by reference will be desirable. In still other embodiments, epicardial electrodes as disclosed in U.S. Pat. No. 3,737,579, issued to Bolduc on Jun. 5, 1973, or in U.S. Pat. No. 4,313,448 issued to Stokes on Feb. 2, 1982, both of which are incorporated herein by reference in their entireties may be used to stimulate the SA or AV nodal fat pads or for atrial or ventricular pacing and sensing. The particular electrode systems illustrated are intended to be exemplary of the general types of electrode systems which may be employed in conjunction with the present invention and are not believed to be critical to successfully practicing the invention.

Figure 3B:
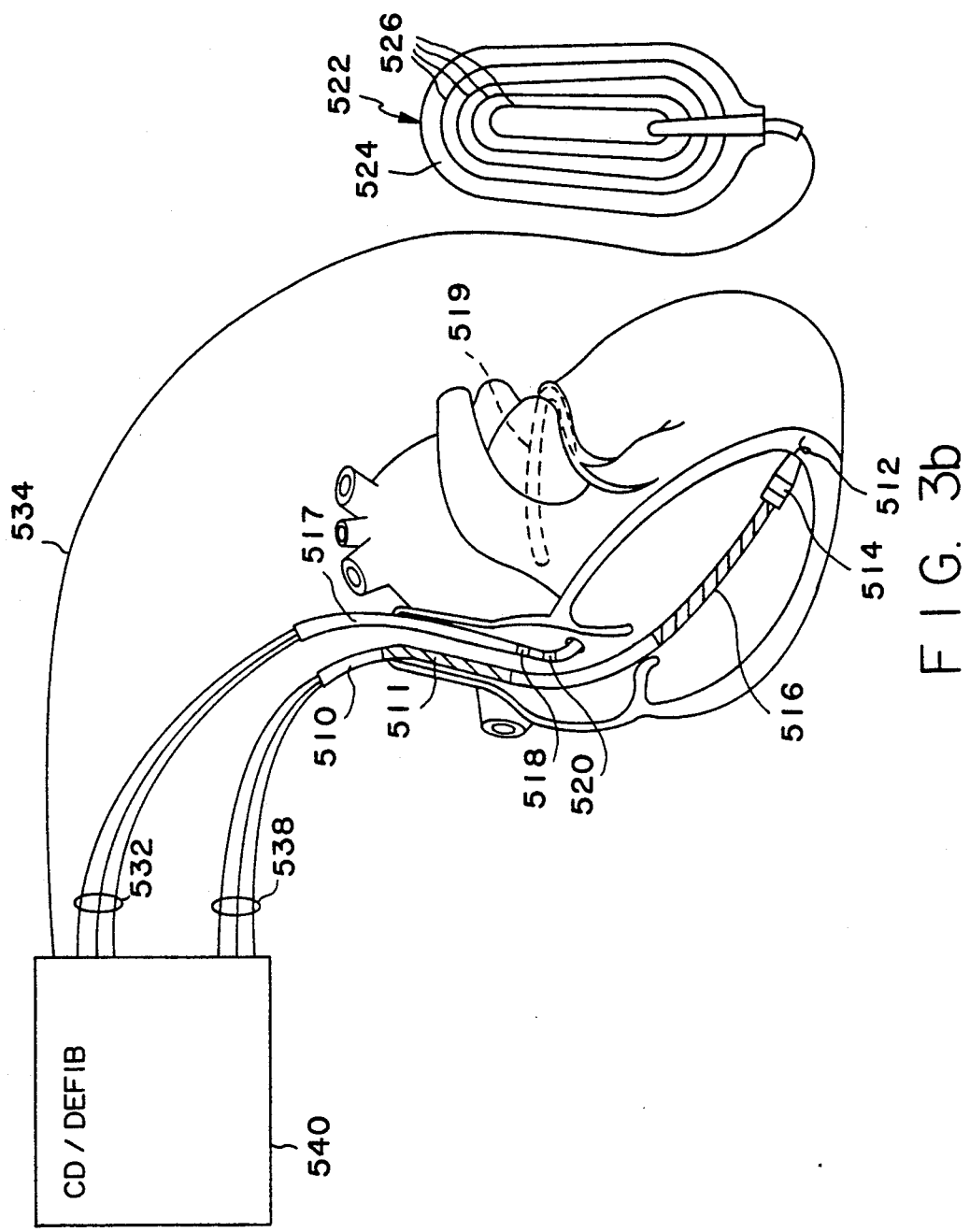

FIG. 3b is a cutaway view of the heart illustrating an implantable cardioverter/defibrillator and associated lead system. A ventricular defibrillation lead 510 carries a bipolar electrode pair located at the right ventricular apex. The electrode pair includes a tip electrode 512, which takes the form of a helical electrode screwed into the right ventricular myocardium and a ring electrode 514. The lead also includes two elongated coiled defibrillation electrodes 511 and 516, located in the superior vena cava and right ventricle, respectively. The illustrated lead corresponds to lead 110, illustrated in FIG. 3a, discussed above, with the addition of electrode 511. Each of the electrodes 511, 512, 514, and 516 is coupled to one of four mutually insulated conductors 538, which connect them to an implanted pacemaker/cardioverter/defibrillator 540.

A coronary sinus lead 517 is provided carrying an elongated defibrillation electrode 519, illustrated in broken outline, located within the coronary sinus and great vein and extending around the heart to approximately the point at which the great vein turns downward toward the apex of the heart. The lead 517 is also provided with two ring electrodes 518 and 520 located within the atrium and intended for use in sensing and pacing in the atrium and may in some cases be useful in simultaneously or individually stimulating the SA and AV nodal fat pads. Electrodes 518, 519 and 520 are each coupled to one of three mutually insulated conductors 532 which couple them to implanted pacemaker/cardioverter/defibrillator 540. Lead 517 may correspond to the coronary sinus/great vein lead 117, illustrated in FIG. 3a, discussed above.

Defibrillation electrodes 511 and 519 may also be useful in some cases for individual stimulation of the SA and AV nodal fat pads, respectively, when paired with a remote electrode These electrodes may also in some cases be useful in simultaneous stimulation of the SA and AV nodal fat pads when paired together.

Subcutaneous lead 522 is implanted in the left chest and includes a large surface electrode pad 524, carrying four elongated electrode coils 526, all coupled to insulated conductor 534, which connects them to defibrillator 540. Electrode 522 corresponds to the electrode 122 illustrated in FIG. 3a, discussed above.

Numerous alternative electrode configurations may be appropriate for stimulation of one or both fat pads. For example, a pair of endocardial electrodes located adjacent the junction of the right atrium and the superior vena cava mat be appropriate for stimulation of the SA nodal fat pad. Alternatively, epicardial or myocardial electrodes applied to or adjacent the SA nodal and/or AV nodal fat pads may be employed. As noted above, combined stimulation of the SA and AV nodal fat pads may also be accomplished using vagal nerve electrodes.

FIG. 4 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverter/ defibrillators having features as disclosed in prior U.S. Pat. No. 4,548,209, issued to Wielders,et al on Oct. 22, 1985, U.S. Pat. No. 4,693,253, issued to Adams et al on Sep. 15, 1987, U.S. Pat. No. 4,830,006, issued to Haluska et al on May 6, 1989 and U.S. Pat. No. 4,949,730, issued to Pless et al on Aug. 21, 1990, all of which are incorporated herein by reference in their entireties.

The device is provided with an electrode system including electrodes as illustrated in FIGS. 3a–3c. An additional electrode 141 may be an indifferent electrode located on the housing of the implantable pacemaker/cardioverter/defibrillator.

Electrodes 612 and 614 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 612 and 614 exceeds the present sensing threshold.

Electrodes 618 and 620 are located on or in the atrium and are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 618 and 620 exceeds the present sensing threshold.

Electrodes 604, 605, 606 and 607 may correspond to individual epicardial, myocardial or endocardial electrode pairs coupled to individually stimulate the FA or AV nodal fat pads, respectively. Electrodes 600, 616, 619 and 626 correspond to epicardial, subcutaneous or endocardial defibrillation electrodes. For example, electrode 600, 616, 619 and 626 may correspond to electrodes 100, 116, 119 and 126 as illustrated in FIG. 3a.

The bandpass characteristics of amplifiers 200 and 204 may be optimized for sensing R-waves and P-waves, respectively. The general operation of the R-wave and P-wave amplifiers 200 and 204 may correspond to that disclosed in commonly assigned, copending U.S. Pat. Application Ser. No. 07/612,760, by Keimel, et al., filed Nov. 15, for an Apparatus for Monitoring Electrical Physiologic Signals, incorporated herein by reference in its entirety. The sensing thresholds defined by amplifiers 200 and 204 may be set to 75% of the detected signal amplitude and preferably decay to a minimum threshold level within three seconds thereafter, similar to the automatic sensing threshold circuitry illustrated in the article "Reliable R-Wave Detection from Ambulatory Subjects", by Thakor et al, published in Biomedical Science Instrumentation, Vol. 4, pp 67-72, 1978, incorporated herein by reference in its entirety. However, in the context of the present invention, it is preferable that the threshold level of R-wave amplifier 200 not be adjusted in response to paced R-waves, but instead should continue to approach the minimum threshold level following paced R-waves to enhance sensing of low level spontaneous R-waves associated with tachyarrhythmias. The invention may also be practiced in conjunction with more traditional P-wave and R-wave amplifiers of the type comprising a band pass amplifier and a comparator circuit to determine when the bandpassed signal exceeds a predetermined, fixed sensing threshold.

Switch matrix 208 is used to select which of the available electrodes are coupled to wide band (0.5-200 Hz) amplifier 210 for use in digital signal analysis and to select which of the electrodes are coupled to the pulse burst generator 232 for stimulation of the AV and/or SA nodal fat pads. The selected electrode pairs for either purpose may comprise any of the illustrated electrodes. However, electrode pairs including at least one of electrodes 612, 614, 618 and 620 will typically be employed as inputs to amplifier 210. Selection of electrodes is controlled by the microprocessor 224 via data-/address bus 218, which selections may be varied as desired to effect sequential, simultaneous or individualized stimulation of the fat pads.

Signals from the electrodes selected for coupling to bandpass amplifier 210 are provided to multiplexer 220, and thereafter converted to multibit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Burst generator 232 may employ any appropriate technology for generation of stimulation pulses in the form of individual pulses or pulse trains, having amplitudes up to 50 ma, pulse widths of up to 2 ms, and frequencies of up to 1000 Hz. For example, the Medtronic Model 2349 Programmable Stimulator, as discussed in the above cited Cooper et al reference includes circuitry for generating appropriate stimulation pulses and trains. Given that circuitry for pulse generation has become well known to those skilled in the art, no detailed disclosure is included herein. The specific timing, amplitude, duration and number of pulses is controlled by microprocessor 224 via data bus 218.

Much of the remainder of the circuitry is dedicated to the provision of cardiac pacing, cardioversion and defibrillation therapies, which for purposes of the present invention may correspond to the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with antitachyarrhythmia pacing in both the atrium and the ventricle, employing any antitachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 226, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on timeout trigger generation of pacing pulses by pacer output circuitry 214 and 216, which are coupled to electrodes 118, 120, 112, 114. The escape interval counters are also reset on generation of pacing pulses, and thereby control the basic timing of cardiac pacing functions, including anti-tachy pacing. The durations of the intervals defined by the escape interval timers are determined by microprocessor 224, via data-/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates as an interrupt driven device, and is awakened by interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, the portion of the memory 226 (FIG. 4) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate detection measuring such factors are described in the above cited U.S. Pat. No. 4,726,380, issued to Vollmann, U.S. Pat. No. 4,880,005, issued to Pless et al and U.S. Pat. No. 4,830,006, issued to Haluska et al. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170. However, one of the advantages of the present invention is that it is believed practicable in conjunction with most prior art tachycardia detection algorithms.

In the event that a tachyarrhythmia is detected, and an antitachyarrhythmia pacing regimen is desired, appropriate timing intervals for controlling generation of antitachy pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of antitachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the an escape interval counter to control timing of such cardioversion and defibrillation pulses, as well as associated refractory periods. In response to the detection of fibrillation or a tachyarrhythmia requiring a cardioversion pulse, microprocessor 224 activates cardioversion/defibrillation control circuitry 230, which initiates charging of the high voltage capacitors 246, 248, 250 and 252 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to VVI pacing and awaits the next successive interrupt due to pacing or the occurrence of a sensed atrial or ventricular depolarization.

One embodiment of an appropriate system for delivery and synchronization of cardioversion and defibrillation pulses and for controlling the timing functions related to them is disclosed in more detail in copending, commonly assigned U.S. Pat. Application Ser. No. 07/612,761, by Keimel, for an Apparatus for Detecting and Treating a Tachyarrhythmia, filed Nov. 15, 1990 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, selection of the particular electrode configuration for delivery of the cardioversion or defibrillation pulses is controlled via output circuit 234, under control of cardioversion/defibrillation control circuitry 230 via control bus 238. Output circuit 234 determines which of the high voltage electrodes 600, 616, 619 and 626 will be employed in delivering the defibrillation or cardioversion pulse regimen, and may also be used to specify a multielectrode, simultaneous pulse regimen or a multielectrode sequential pulse regimen. Monophasic or biphasic pulses may be generated. Generally, defibrillation and cardioversion regimens involving three of the high voltage electrodes 600, 616, 619 and 626 will be employed to accomplish ventricular defibrillation. Examples of such multiple electrode pulse regimens may be found in the above cited patent issued to Mehra and in U.S. Pat. No. 4,727,877, issued on May 1, 1988 to Kallok et al, incorporated by reference in its entirety. Atrial defibrillation will generally be accomplished using electrode 610, located in the superior vena cava in conjunction with one of the other high voltage electrodes, preferably electrode 619, located in the coronary sinus and great vein.

One example of circuitry which may be used to select electrode configuration in conjunction with delivery of monophasic pulses is set forth in commonly assigned copending U.S. Pat. Application Ser. No. 07/612,758, filed by Keimel, for an Apparatus for Delivering Single and Multiple Cardioversion and Defibrillation Pulses, filed Nov. 14, 1990, incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses. Monophasic pulse regimens employing only a single electrode pair according to any of the above cited references which disclose implantable cardioverters or defibrillators may also be used.

In modern implantable cardioverter/defibrillators, the particular therapies are programmed into the device ahead of time by the physician, and a menu of therapies is typically provided. For example, on initial detection of an atrial or ventricular tachycardia, an antitachycardia pacing therapy may be selected and delivered to the chamber in which the tachycardia is diagnosed or to both chambers. On redetection of tachycardia, a more aggressive antitachy pacing therapy may abe scheduled. If repeated attempts at antitachy pacing therapies fail, a higher level cardioversion pulse may be selected thereafter. Therapies for ventricular tachycardia may also vary with the rate of the detected tachycardia, with the therapies increasing in aggressiveness as the rate of the detected tachycardia increases. For example, fewer attempts at antitachy pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, the typical therapy will be delivery of a high amplitude defibrillation pulse, typically in excess of 20 joules in the case of ventricular fibrillation and in excess of 10 joules in the case of atrial defibrillation. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of antitachyarrhythmia therapies include the above-cited U.S. Pat. No. 4,830,006, issued to Haluska, et al, U.S. Pat. No. 4,727,380, issued to Vollmann et al and U.S. Pat. No. 4,587,970, issued to Holley et al.

FIGS. 5a–5e are functional flow charts representing the operation of the device illustrated in FIG. 4, in conjunction with the sinus/non-sinus and ventricular/supraventricular tachycardia discrimination functions of the present invention. FIGS. 5a–5e are intended to functionally represent that portion of the software employed by microprocessor 224 (FIG. 4) which implements the discrimination function.

The flow charts 5a–5e all are entered following an interrupt indicating pacing or sensing and storage of the intervals exiting with the interrupt. The first functional step in flow charts 5a–5c and 5e is the determination of the presence of a ventricular fibrillation, using one or more any of the detection methodologies known to the art, as discussed above. In these flowcharts, the second step is typically the detection of a ventricular rate which is indicative of the occurrence of a tachycardia. Again, this step may be accomplished using any of the methods for detection of high ventricular rates known to the art. Similarly, several of the flow charts include the step of detection of a high atrial rate. This step may also correspond to any of the atrial rate detection methodologies known to the art, used to diagnose the presence of a tachycardia based on high atrial rate.

In the flowcharts as illustrated, use of fat pad stimulation to determine the origin of a detected tachyarrhythmia may be initiated in direct response to detection of ventricular and/or atrial rates indicative of the occurrence of tachycardia. This allows the use of the invention in devices having only atrial or only ventricular sensing capability.

However, it is also envisioned that in many cases the invention will be practiced in devices as illustrated in FIG. 4, having both atrial and ventricular sensing capabilities. In such embodiments, initiation of the fat pad stimulation function will occur only when analysis of preceding stored R-R, P-R and P-P intervals is ineffective to determine the origin of the tachyarrhythmia. For example, the presence of simultaneous high, equal atrial and ventricular rates as illustrated in FIGS. 1a, 1c and 1d may be substituted for the "HIGH V-RATE?" decision step in FIGS. 5a, 5b, 5c or 5e. Alternatively, the mere simultaneous presence of high atrial and ventricular rates as illustrated in FIG. 1b may be employed as the criterion for activating burst stimulation.

For purposes of reading the flowcharts, it should be assumed therefore that the step indicated as "HIGH V-RATE" may be either the simple detection of a tachycardia in the ventricle or may be the detection of a tachycardia in the ventricle under circumstances in which analysis of the timing of the atrial and ventricular depolarizations does not unambiguously identify the origin of the tachycardia.

Figure 5A:
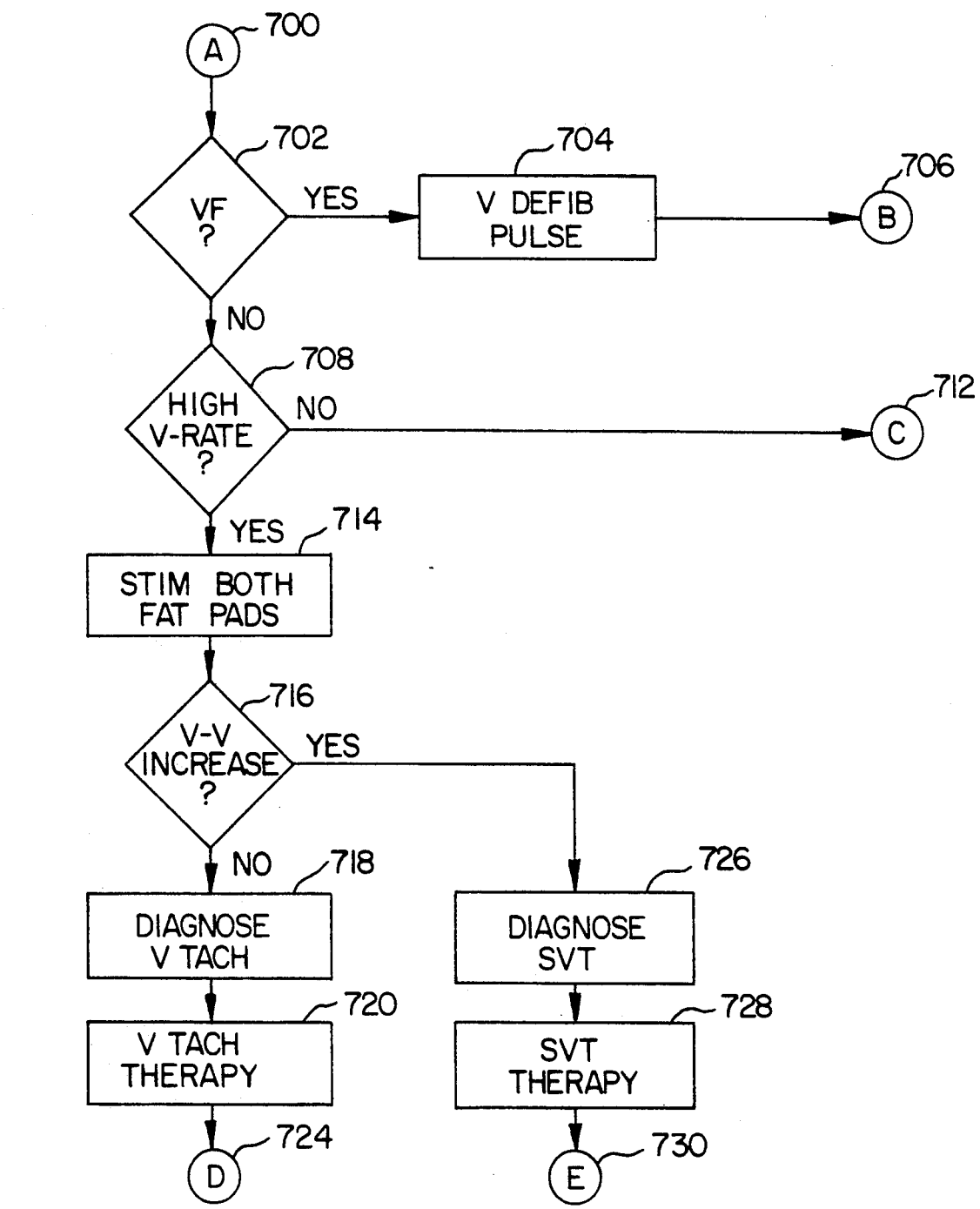
FIGS. 5a, 5b, 5c, 5d and 5e are functional flow charts illustrating the methods of discrimination between ventricular tachycardia and supraventricular tachycardia and for discriminating between sinus and non-sinus tachycardia provided by the present invention, as embodied in the device illustrated in FIG. 4.

In FIG. 5a, the flow chart is entered at 700, in response to a sense interrupt. The available stored intervals (e.g. R-R, P-R, R-P, P-P) ending on the interrupt are stored and analyzed. At 702, the device checks to determine whether a ventricular fibrillation is present, which step may be accomplished using ventricular fibrillation detection algorithms known to the art. If ventricular fibrillation is detected, a defibrillation pulse is delivered at 704, and the device returns to bradycardia pacing mode at 706, attempting to determine whether fibrillation has successfully been terminated.

In the event that fibrillation is not detected, the stored intervals are analyzed at 708 to determine whether a ventricular rate indicative of a tachycardia is present, and optionally whether the origin of the high rate is ambiguous, as discussed above. If no such tachycardia is diagnosed, the device returns to bradycardia pacing mode at 712.

In the event that such a tachycardia is diagnosed at 708, the device provides simultaneous stimulation to both fat pads at 714, synchronized to sensed atrial depolarizations, if the device has the capability of sensing the atrial EGM, or synchronized to the ventricular EGM, if not. Thereafter, the V-V interval is analyzed at 716 to determine whether it there has been an increase in the V-V interval following stimulation of the fat pads. If no increase in the R-R interval is detected, the tachycardia is diagnosed as being of ventricular origin at 718, and an appropriate therapy for termination of ventricular tachycardia is delivered at 720, and the device returns to bradycardia pacing mode at 724, and attempts to determine whether the delivered therapy was effective in terminating the tachyarrhythmia.

If an R-R interval increase is detected at 716 following fat pad stimulation, the tachycardia is diagnosed as being supra ventricular in origin. Further analysis of stored intervals is undertaken to determine the appropriate supra ventricular tachycardia therapy, which is delivered at 728. The device then returns to bradycardia pacing at 730 and attempts to determine whether the delivered therapy was effective in terminating the detected tachycardia.

If the device is provided with means for monitoring the atrial EGM, the device may also check to determine whether the P-R and P-P intervals following burst stimulation were prolonged as part of the diagnosis of the supraventricular tachycardia at 726. If the P-P interval was prolonged, the device may diagnose a sinus tachycardia, and the appropriate "SVT THERAPY" delivered at 728 may be no therapy. In the absence of P-P interval prolongation, the tachycardia is presumed to be treatable, with antitachycardia pacing, cardioversion or defibrillation being delivered, depending on the timing of the sensed depolarizations.

As illustrated in FIG. 1b, in some cases, it may be advantageous to activate the burst stimulation function even when the atrial rate is known to exceed the ventricular rate, in order to distinguish simultaneous tachyarrhythmias in the atrium and ventricle from atrial tachycardias conducted less than 1:1 to the ventricle. In such cases, an increase in the degree of A-V block may be used to identify the supraventricular origin of the tachycardia at 716, as an alternative to prolongation of the R-R interval.

Figure 5B:
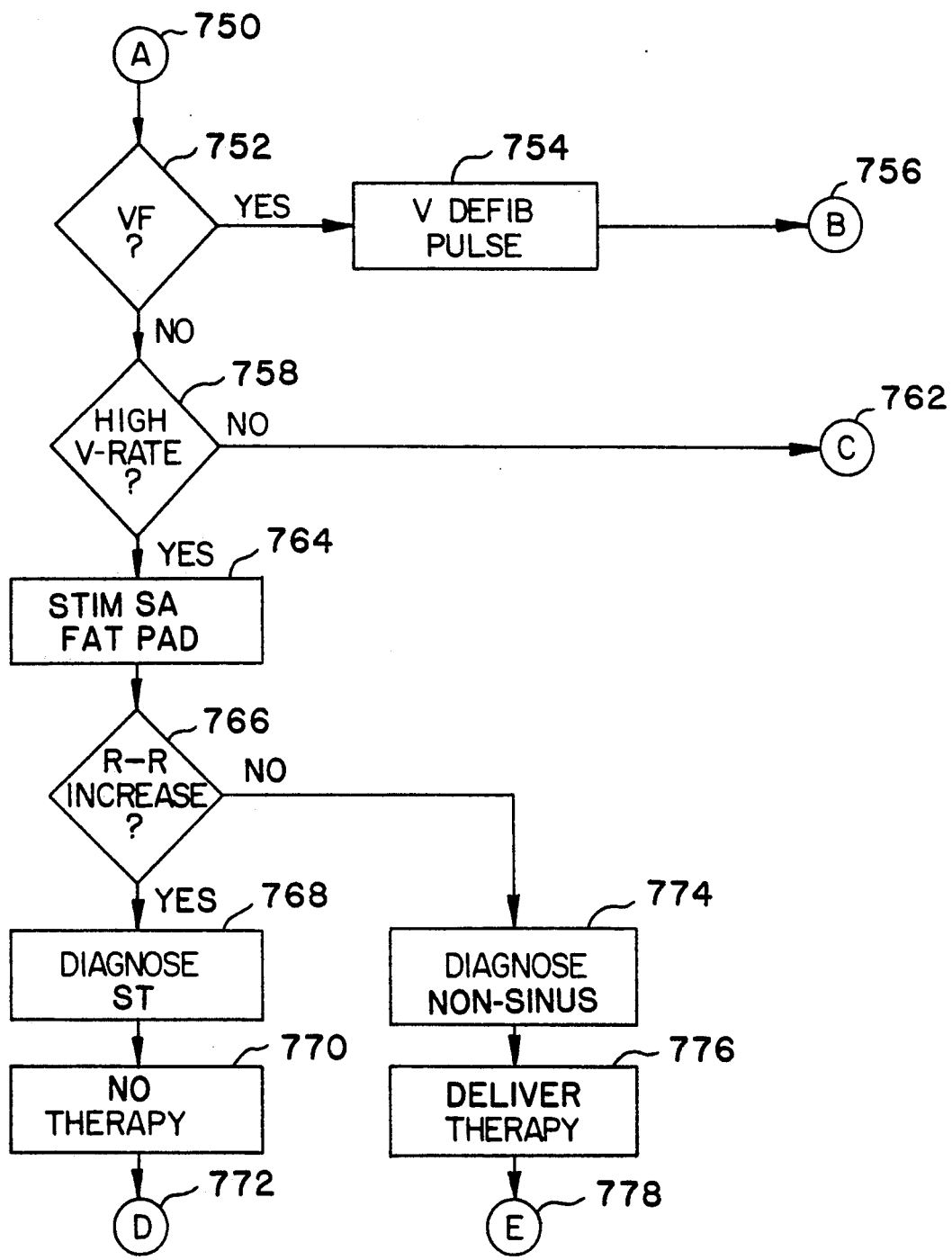

FIG. 5b illustrates the operation of a device provided with the ability to individually stimulate the SA nodal fat pad. The flow chart is entered at 750 on occurrence of a sensed atrial or ventricular contraction. Analysis of stored intervals is undertaken at 752 to determine whether ventricular fibrillation is present. If present, a ventricular defibrillation pulse is delivered at 754 and the device returns to bradycardia pacing mode at 756, attempting to determine whether the defibrillation pulse was effective in terminating the detected fibrillation.

If fibrillation is not detected, the stored intervals are analyzed at 758 to determine whether a ventricular rate indicative of tachycardia is present. If not, the device returns to bradycardia pacing mode at 762. In the event that a tachycardia appropriate for activation of burst stimulation is detected at 758, stimulation of the SA nodal fat pad, synchronized to one or more detected atrial depolarizations is undertaken at 764. At 766, the device checks to see whether a corresponding increase in R-R interval resulted. In the even that an R-R interval increase occurred, the arrhythmia is diagnosed as sinus tachycardia at 768, no therapy is delivered at 770, and the device returns to bradycardia pacing at 772.

If, on the other hand, an R-R increase was not detected, the rhythm will be diagnosed as a non-sinus tachycardia at 774, and based upon analysis of the stored intervals, an appropriate therapy is delivered at 776. The device then returns to bradycardia pacing mode at 778. The embodiment of FIG. 5b may alternatively measure P-P intervals at 766 to determine whether a sinus tachycardia is present, as discussed above in conjunction with the description of FIG. 5a.

Figure 5C:
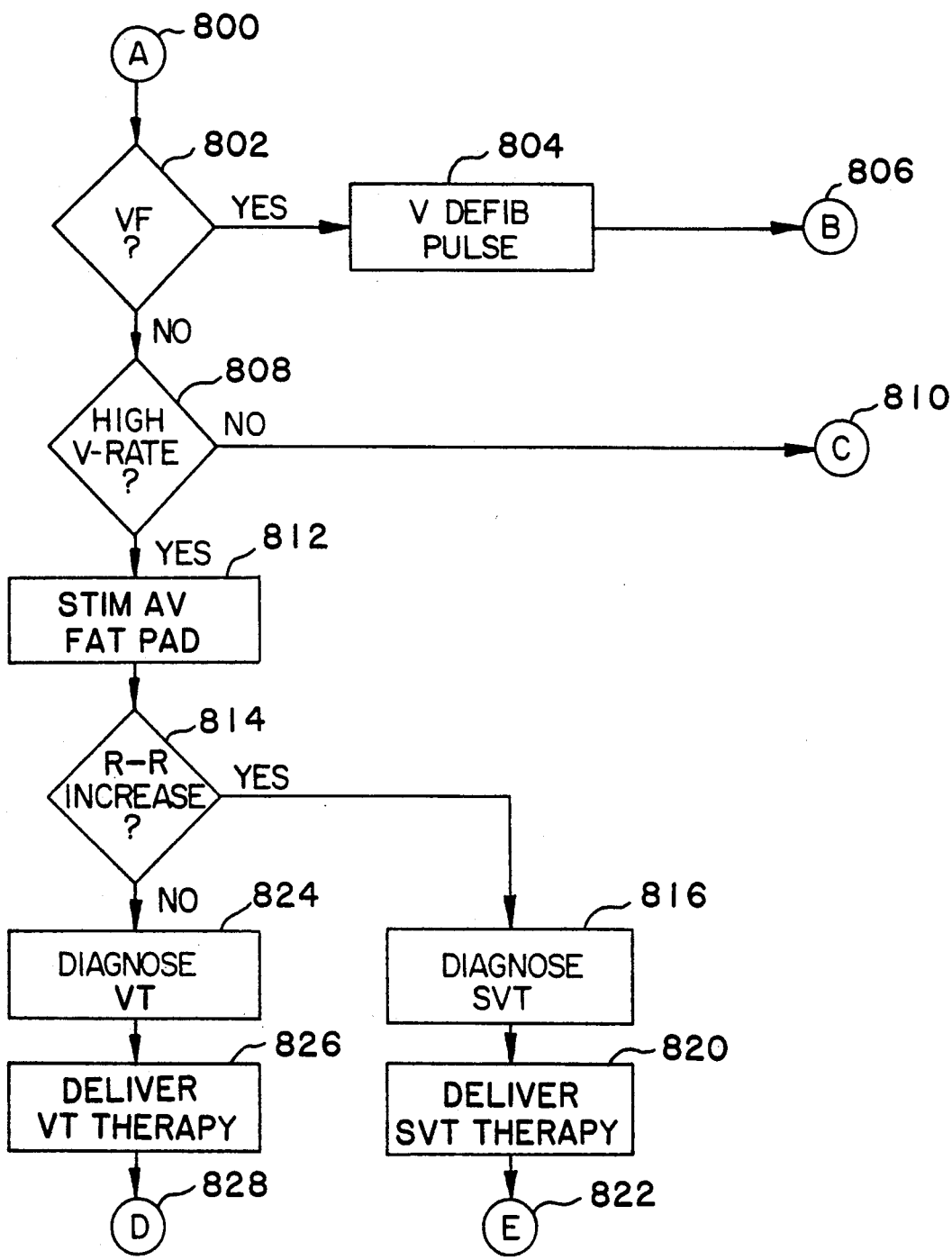

FIG. 5c illustrates the functioning of an embodiment of the invention provided with an electrode set for individually stimulating the AV nodal fat pad. As in FIGS. 5a and 5b, the flow chart is entered at 800 in response to a sensed or paced event, the stored intervals are analyzed to determine the presence of ventricular fibrillation at 802, a fibrillation pulse is delivered if appropriate at 806, and the device returns to bradycardia pacing at 808. If fibrillation is not detected, the stored intervals are analyzed at 810 to determine whether a ventricular rate indicative of a tachycardia is present at 810. If not, the device returns to bradycardia pacing at 812.

In the event that a ventricular rate indicative of tachycardia is detected at 810, the AV nodal fat pad is stimulated at 812. The stimulation may be synchronized to detected ventricular contractions. However, in some circumstances, it may be desirable to synchronize the stimulation to atrial contractions, if testing indicates that induction of atrial fibrillation is a problem. The device checks at 814 to determine whether the AV nodal fat pad stimulation resulted in an increased R-R interval. If so, the tachycardia is diagnosed as supraventricular tachycardia at 816, the rhythm is further analyzed at 818, and an appropriate therapy is delivered at 820. If no R-R interval increase results, the tachycardia is diagnosed as ventricular tachycardia at 824, and appropriate ventricular tachycardia therapy is delivered at 826, and the device returns to bradycardia pacing at 828.

Figure 5D:
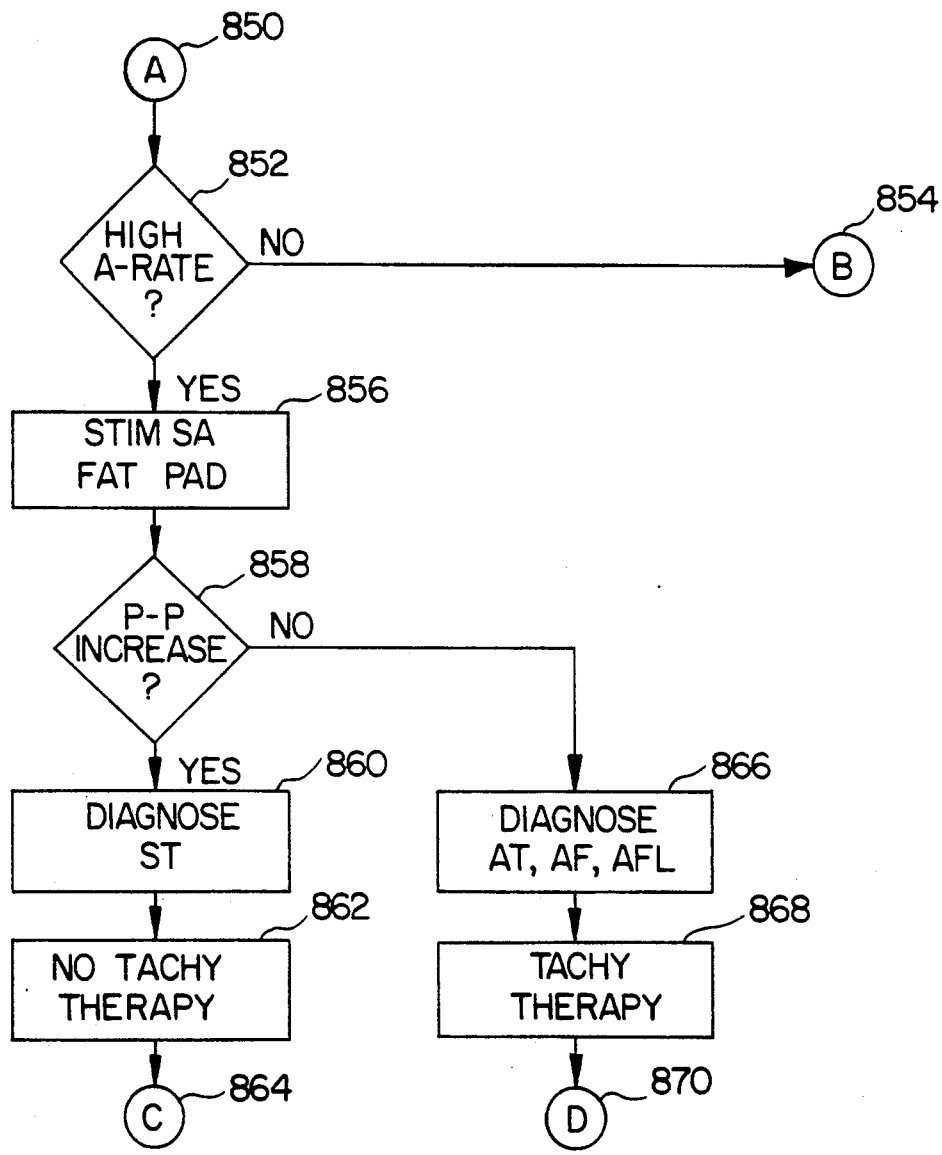

FIG. 5d illustrates an embodiment of a device adapted for use in conjunction with a device which includes an atrial antitachycardia pacemaker/cardioverter. Again, the flow chart is entered at 850 in response to sensing of an atrial depolarization or delivery of an atrial pacing pulse. The stored intervals are analyzed at 852 to determine whether an atrial rate indicative of a tachycardia is present. If not, the device continues to pace as a bradycardia pacemaker in the atrium at 854.

If an atrial rhythm is detected indicative of tachycardia, stimulation of the SA nodal fat pad is undertaken at 856, and the device checks at 858 to determine whether a corresponding increase in P-P interval has occurred. If so, the tachycardia is diagnosed as a sinus tachycardia at 860, no therapy is delivered at 862, and the device returns to functioning as a bradycardia pacer at 864. If, on the other hand, no increase in P-P interval is detected, the device diagnoses the rhythm as atrial tachycardia, flutter or fibrillation at 866, and an appropriate tachycardia therapy is delivered at 868. The device then returns to bradycardia pacing at 870. As an alternative, the device could also measure the R-R intervals following burst stimulation to determine whether the rhythm is of sinus origin, as would be indicated by an increase in R-R interval.

The flow chart of FIG. 5d is also applicable to an embodiment of the invention which includes a dual chamber cardiac pacemaker, as discussed in conjunction with FIG. 1e, above. In such case, the criteria for activating the burst function should be an atrial rate which could be the result of either tachycardia or sinus rhythm, e.g. 150–180 bpm or greater. In such case, the therapy delivered at 868 would be cardiac pacing in a non-atrial synchronous mode, e.g. VVI or DDI. If the high atrial rate is determined to be of sinus origin, no change in pacing mode would occur, and at 862, the device would simply continue to pace in an atrial synchronous mode, as discussed above in conjunction with FIG. 1e.

Figure 5E:
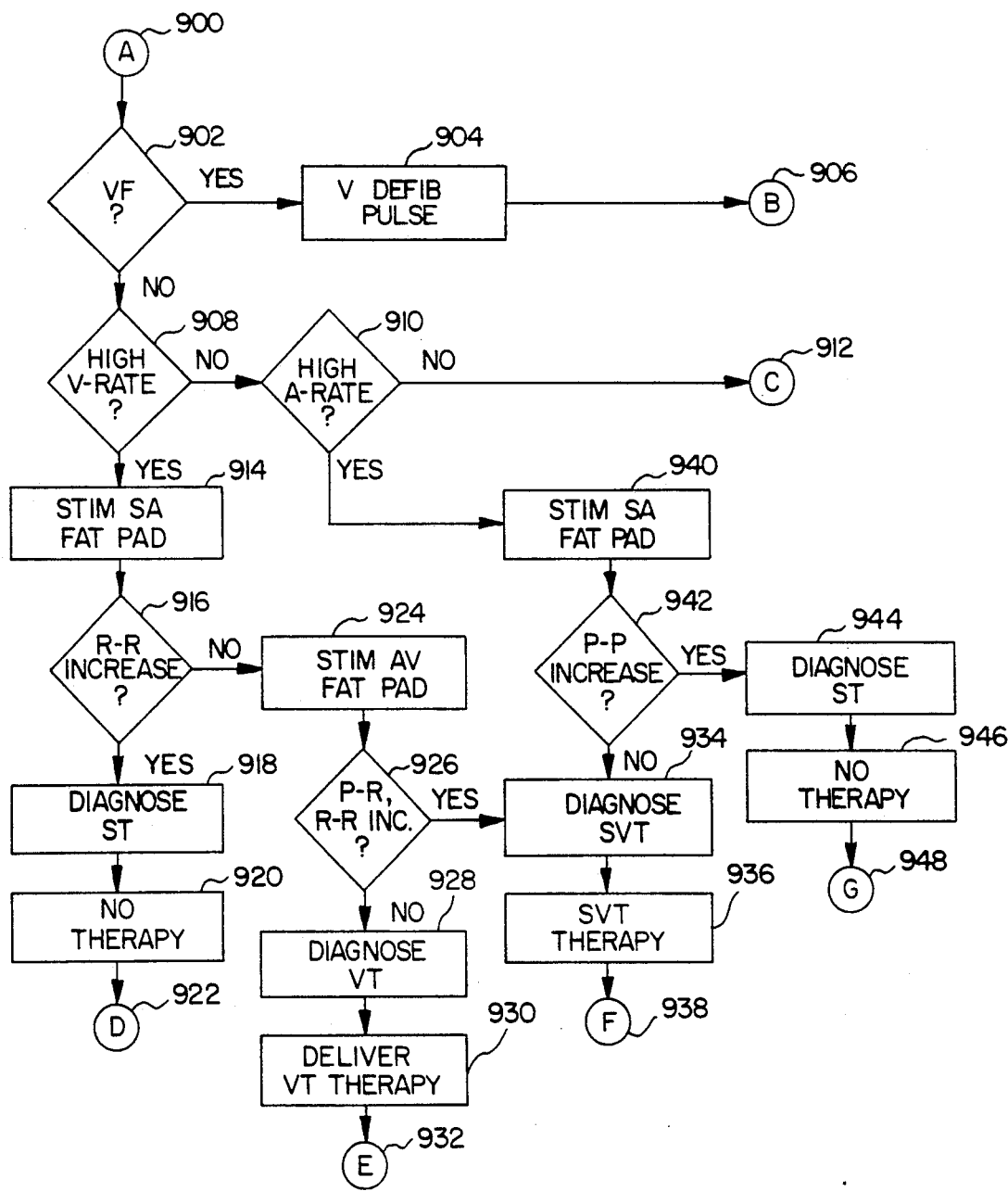

FIG. 5e illustrates the operation of a device including electrodes capable of individually stimulating the SA and AV nodal fat pads. As in FIGS. 5a–5d, the flow chart is entered at 900 in response to a sense or pace event. The stored intervals are analyzed at 902 to determine whether ventricular fibrillation is present. If so, a ventricular defibrillation pulse is delivered at 904, and the device returns to bradycardia pacing at 906.

If fibrillation is not present, the stored intervals are checked to determine whether a ventricular rate indicative of tachycardia is present at 908. If not, the atrial rate is checked to determine whether a rhythm indicative of tachycardia is present at 910. If not, the device returns to bradycardia pacing at 912.

In the event that a ventricular rate indicative of tachycardia is detected at 908, the SA nodal fat pad is stimulated at 914, synchronized to one or more sensed atrial depolarizations. The R-R interval is checked at 916 to determine whether an increase in R-R interval has resulted. If an increased R-R interval occurs, the rhythm is diagnosed as sinus tachycardia at 918, no therapy is delivered at 920, and the device returns to bradycardia pacing mode at 922. As an alternative, the device could instead check for an increased P-P interval at 916.

If an increase in R-R (or P-P) interval is not detected at 916 following SA nodal fat pad stimulation, the AV nodal fat pad is individually stimulated at 924. The device checks at 926 to determine whether an increase in the P-R or R-R interval resulted from stimulation. If not, the device diagnoses the tachycardia as ventricular tachycardia at 928, an appropriate ventricular tachycardia therapy is delivered at 930, and the device returns to bradycardia pacing at 932.

If an increase in P-R or R-R interval is detected at 926, the device diagnoses the tachycardia as being supraventricular tachycardia at 934, analyzing the stored intervals to further refine the diagnosis, and deliver an appropriate SVT antitachycardia pacing or cardioversion therapy at 936. The device then returns to bradycardia pacing mode at 938.

In the event that a high atrial rate is detected at 910 in the absence of a high ventricular rate, SA nodal fat pad stimulation may be undertaken at 940, and the P-P (or R-R) interval checked at 942 to determine whether fat pad stimulation resulted in a prolongation of the P-P interval. If so, the high atrial rate is diagnosed as being the result of sinus tachycardia at 944, no antitachycardia therapy is delivered at 946, and the device returns to bradycardia pacing at 948. If, on the other hand, an increased P-P interval is not diagnosed, an atrial tachycardia, atrial flutter or other supraventricular arrhythmia is diagnosed at 934. Further analysis of the stored intervals is undertaken and delivery of an appropriate SVT pacing or cardioversion therapy is undertaken at 936. The device then returns to bradycardia pacing mode at 938.

The above flow charts are intended to be examples of mechanisms for incorporating the diagnostic power of the present invention into automated antitachycardia systems, such as implantable pacemaker/cardioverter/-defibrillators. By choosing appropriate activation criteria for fat pad stimulation and appropriately processing the interval changes, or the lack thereof that result, a substantial improvement in the accuracy of diagnosis can be obtained. Delivery of therapy where it is destined to be ineffective, such as in the case of sinus tachycardia, can be avoided. Distinction between ventricular and supraventricular tachycardias may also be accomplished, along for a more focused approach to delivery of therapy to terminate the arrhythmia. This particularly beneficial in the context of devices which employ atrial antitachy pacing and/or cardioversion capabilities, allowing for localized delivery of pacing or cardioversion therapy to terminate atrial tachycardias, including atrial flutter.

Due to overlap in appropriate therapy types for some forms of ventricular and supraventricular tachycardias, it is not to be understood that in every case, discrimination between ventricular and supraventricular origin of tachycardia will necessarily result in a different therapy being delivered. However, it is believed that in practical embodiments of the invention, different therapy menus may be available for ventricular and supraventricular tachycardias, setting forth therapy sequences and types which may vary in their degree of aggressiveness, and in the number of pacing therapies tried prior to attempting cardioversion or defibrillation, depending upon the diagnosis of the origin of the tachycardia.

While the therapies discussed in conjunction with the disclosed embodiment generally relate to delivery of electrical pulses, it should be understood that the invention may be usefully practiced in conjunction with any device adapted to deliver differing therapies for tachycardia and fibrillation, including drug therapies, non-pulsatile electrical therapies, and any other such therapies as may be implemented in such devices as their development progresses, whether applied directly to the heart or systemically. Similarly, it should be understood that the discriminator of the present invention, while particularly adapted for use in or in conjunction with an implantable pacemaker/cardioverter/defibrillator may also in some cases be usefully practiced in conjunction with a non-implantable device, in a device which, for example only treats fibrillation or only treats tachycardia, or even in a device adapted primarily for diagnostic purposes.

In conjunction with the above application, I claim:

1. A method of discriminating between a rapid heart rhythm of ventricular origin and rapid heart rhythm of supraventricular origin, comprising:
   monitoring the occurrence of depolarizations of said heart;
   measuring the rate of said monitored depolarizations;
   electrically stimulating the fat pad or fat pads associated with the SA node and/or the AV node of said heart if a rapid heart rhythm is detected;
   determining whether stimulating said fat pad or fat pads results in a change in said detected rapid rhythm of said heart; and
   diagnosing whether said detected rapid heart rhythm is of a ventricular or a supraventricular origin as a function of whether stimulating said fat pad or pads results in a change in said detected rapid rhythm of said heart.

2. A method according to claim 1, wherein said determining step comprises determining whether the rate of depolarization of the ventricles of said heart is slowed as a result of stimulation of said fat pad or pads.

3. A method according to claim 1, wherein said determining step comprises determining whether the rate of depolarization of the atria of said heart is slowed as a result of stimulation of said fat pad or pads.

4. A method according to claim 1, wherein said determining step comprises determining whether the interval separating depolarizations of the atria of said heart from depolarizations of the ventricles of said heart is extended as a result of stimulation of said fat pad or pads.

5. A method according to claim 1 wherein said determining step comprises determining the percentage of depolarizations of the atria of said heart leading to depolarizations of the ventricles of said heart and for determining whether said percentage is reduced as a result of stimulation of said fat pad or pads.

6. A method according to claim 1 wherein said stimulating step comprises stimulation of said fat pad or pads by means of one or more electrical pulses synchronized to the detected depolarizations of the atrium of said heart.

7. A method according to claim 1 wherein said stimulating step comprises stimulation of said fat pad or pads by means of one or more electrical pulses synchronized to the detected depolarizations of the ventricle of said heart.

8. A method of discriminating between a rapid heart rhythm of sinus origin and rapid heart rhythm of non-sinus origin, comprising:
   monitoring the occurrence of depolarizations of said heart;
   measuring the rate of said monitored depolarizations;
   electrically stimulating the fat pad associated with the SA node of said heart if a rapid heart rhythm is detected;
   determining whether stimulating said fat pad results in a change in said detected rapid rhythm of said heart; and
   diagnosing whether said detected rapid heart rhythm is of a sinus or a non-sinus origin as a function of whether stimulating said fat pad or pads results in a change in said detected rapid rhythm of said heart.

9. A method according to claim 8, wherein said determining step comprises determining whether the rate of depolarization of the ventricles of said heart is slowed as a result of stimulation of said fat pad.

10. A method according to claim 8, wherein said determining step comprises determining whether the rate of depolarization of the atria of said heart is slowed as a result of stimulation of said fat pad.

11. A method according to claim 8 wherein said stimulating step comprises stimulation of said fat pad or pads by means of one or more electrical pulses synchronized to the detected depolarizations of the atrium of said heart.

12. A method of treating tachycardias in a heart, comprising:
monitoring the occurrence of depolarizations of said heart;
measuring the rate of said monitored depolarizations;
electrically stimulating the fat pad or fat pads associated with the SA node and/or the AV node of said heart if a rapid heart rhythm is detected;
determining whether stimulating said fat pad or fat pads results in a change in said detected rapid rhythm of said heart;
diagnosing whether said detected rapid heart rhythm is of a ventricular or a supraventricular origin as a function of whether stimulating said fat pad or pads results in a change in said detected rapid rhythm of said heart;
selecting a therapy to be delivered to said heart as a function of said diagnosing step; and
delivering said selected therapy.

13. A method according to claim 12, wherein said determining step comprises determining whether the rate of depolarization of the ventricles of said heart is slowed as a result of stimulation of said fat pad or pads.

14. A method according to claim 12, wherein said determining step comprises determining whether the rate of depolarization of the atria of said heart is slowed as a result of stimulation of said fat pad or pads.

15. A method according to claim 12, wherein said determining step comprises determining whether the interval separating depolarizations of the atria of said heart from depolarizations of the ventricles of said heart is extended as a result of stimulation of said fat pad or pads.

16. A method according to claim 12, wherein said determining step comprises determining the percentage of depolarizations of the atria of said heart leading to depolarizations of the ventricles of said heart and for determining whether said percentage is reduced as a result of stimulation of said fat pad or pads.

17. A method according to claim 12 wherein said stimulating step comprises stimulation of said fat pad or pads by means of one or more electrical pulses synchronized to the detected depolarizations of the atrium of said heart.

18. A method according to claim 12 wherein said stimulating step comprises stimulation of said fat pad or pads by means of one or more electrical pulses synchronized to the detected depolarizations of the ventricle of said heart.

19. A method of treating tachycardias in a heart, comprising:
monitoring the occurrence of depolarizations of said heart;
measuring the rate of said monitored depolarizations;
electrically stimulating the fat pad associated with the SA node of said heart if a rapid heart rhythm is detected;
determining whether stimulating said fat pad results in a change in said detected rapid rhythm of said heart;
diagnosing whether said detected rapid heart rhythm is of a sinus or a non-sinus origin as a function of whether stimulating said fat pad or pads results in a change in said detected rapid rhythm of said heart;
selecting a therapy to be delivered to said heart as a function of said diagnosing step; and
delivering said selected therapy.

20. A method according to claim 19, wherein said determining step comprises determining whether the rate of depolarization of the ventricles of said heart is slowed as a result of stimulation of said fat pad.

21. A method according to claim 19, wherein said determining step comprises determining whether the rate of depolarization of the atria of said heart is slowed as a result of stimulation of said fat pad.

22. A method according to claim 19 wherein said stimulating step comprises stimulation of said fat pad or pads by means of one or more electrical pulses synchronized to the detected depolarizations of the atrium of said heart.

23. Apparatus for discriminating between a rapid heart rhythm of ventricular origin and rapid heart rhythm of supraventricular origin, comprising:
means for monitoring the occurrence of depolarizations of said heart;
means for measuring the rate of said monitored depolarizations;
means for electrically stimulating the fat pad or fat pads associated with the SA node and/or the AV node of said heart if a rapid heart rhythm is detected;
means for determining whether stimulating said fat pad or fat pads results in a change in said detected rapid rhythm of said heart; and
means for diagnosing whether said detected rapid heart rhythm is of a ventricular or a supraventricular origin as a function of whether stimulating said fat pad or pads results in a change in said detected rapid rhythm of said heart.

24. An apparatus according to claim 23, wherein said determining means comprises means for determining whether the rate of depolarization of the ventricles of said heart is slowed as a result of stimulation of said fat pad or pads.

25. An apparatus according to claim 23, wherein said determining means comprises means for determining whether the rate of depolarization of the atria of said heart is slowed as a result of stimulation of said fat pad or pads.

26. An apparatus according to claim 23, wherein said determining means comprises means for determining whether the interval separating depolarizations of the atria of said heart from depolarizations of the ventricles of said heart is extended as a result of stimulation of said fat pad or pads.

27. An apparatus according to claim 23 wherein said determining means comprises means for determining the percentage of depolarizations of the ventricles of said heart and for determining whether said percentage is reduced as a result of stimulation of said fat pad or pads.

28. An apparatus according to claim 23 wherein said stimulating means comprises means for stimulation of said fat pad or pads by means of one or more electrical pulses synchronized to the detected depolarizations of the atrium of said heart.

29. An apparatus according to claim 23 wherein said stimulating means comprises means for stimulation of said fat pad or pads by means of one or more electrical pulses synchronized to the detected depolarizations of the ventricle of said heart.

30. An apparatus for discriminating between a rapid heart rhythm of sinus origin and rapid heart rhythm of non-sinus origin, comprising:
means for monitoring the occurrence of depolarizations of said heart;
means for measuring the rate of said monitored depolarizations;
means for electrically stimulating the fat pad associated with the SA node of said heart if a rapid heart rhythm is detected;
means for determining whether stimulating said fat pad results in a change in said detected rapid rhythm of said heart; and
means for diagnosing whether said detected rapid heart rhythm is of a sinus or a non-sinus origin as a function of whether stimulating said fat pad or pads results in a change in said detected rapid rhythm of said heart.

31. An apparatus according to claim 30, wherein said determining means comprises means for determining whether the rate of depolarization of the ventricles of said heart is slowed as a result of stimulation of said fat pad.

32. An apparatus according to claim 30, wherein said determining means comprises means for determining whether the rate of depolarization of the atria of said heart is slowed as a result of stimulation of said fat pad.

33. An apparatus according to claim 30 wherein said stimulating means comprises means for stimulation of said fat pad or pads by means of one or more electrical pulses synchronized to the detected depolarizations of the atrium of said heart.

34. An apparatus for treating tachycardias in a heart, comprising:
means for monitoring the occurrence of depolarizations of said heart;
means for measuring the rate of said monitored depolarizations;
means for electrically stimulating the fat pad or fat pads associated with the SA node and/or the AV node of said heart if a rapid heart rhythm is detected;
means for determining whether stimulating said fat pad or fat pads results in a change in said detected rapid rhythm of said heart;
means for diagnosing whether said detected rapid heart rhythm is of a ventricular or a supraventricular origin as a function of whether stimulating said fat pad or pads results in a change in said detected rapid rhythm of said heart;
means for selecting a therapy to be delivered to said heart as a function of said diagnosing step; and
means for delivering said selected therapy.

35. An apparatus according to claim 34, wherein said determining means comprises means for determining whether the rate of depolarization of the ventricles of said heart is slowed as a result of stimulation of said fat pad or pads.

36. An apparatus according to claim 34, wherein said determining means comprises means for determining whether the rate of depolarization of the atria of said heart is slowed as a result of stimulation of said fat pad or pads.

37. An apparatus according to claim 34, wherein said determining means comprises means for determining whether the interval separating depolarizations of the atria of said heart from depolarizations of the ventricles of said heart is extended as a result of stimulation of said fat pad or pads.

38. An apparatus according to claim 34, wherein said determining means comprises means for determining the percentage of depolarizations of the atria of said heart leading to depolarizations of the ventricles of said heart and for determining whether said percentage is reduced as a result of stimulation of said fat pad or pads.

39. An apparatus according to claim 34 wherein said stimulating means comprises means for stimulation of said fat pad or pads by means of one or more electrical pulses synchronized to the detected depolarizations of the atrium of said heart.

40. An apparatus according to claim 34 wherein said stimulating means comprises stimulation of said fat pad or pads by means of one or more electrical pulses synchronized to the detected depolarizations of the ventricle of said heart.

41. An apparatus for treating tachycardias in a heart, comprising:
means for monitoring the occurrence of depolarizations of said heart;
means for measuring the rate of said monitored depolarizations;
means for electrically stimulating the fat pad associated with the SA node of said heart if a rapid heart rhythm is detected;
means for determining whether stimulating said fat pad results in a change in said detected rapid rhythm of said heart;
means for diagnosing whether said detected rapid heart rhythm is of a sinus or a non-sinus origin as a function of whether stimulating said fat pad or pads results in a change in said detected rapid rhythm of said heart;
means for selecting a therapy to be delivered to said heart as a function of said diagnosing step; and
means for delivering said selected therapy.

42. An apparatus according to claim 41, wherein said determining means comprises determining whether the rate of depolarization of the ventricles of said heart is slowed as a result of stimulation of said fat pad.

43. An apparatus according to claim 41, wherein said determining means comprises means for determining whether the rate of depolarization of the atria of said heart is slowed as a result of stimulation of said fat pad.

44. An apparatus according to claim 41 wherein said stimulating means comprises means for stimulation of said fat pad or pads by means of one or more electrical pulses synchronized to the detected depolarizations of the atrium of said heart.

* * * * *

UNITED STATES PATENT AND TRADEMARK OFFICE
CERTIFICATE OF CORRECTION

PATENT NO. : 5,243,980
DATED : September 14, 1993
INVENTOR(S) : Rahul Mehra

It is certified that error appears in the above-indentified patent and that said Letters Patent is hereby corrected as shown below:

Column 5, Line 59, delete "11", and insert in its place --100--.

Column 6, Line 12, delete "11", and insert in its place --110--.

Column 6, Line 41, delete "March 30, 1999, and insert in its place -- March 20, 1991--.

Column 8, Line 1, delete "mat", and insert in its place --may--.

Column 8, Line 51, delete "FA", and insert in its place --SA--.

Column 12, Line 60, delete "abe", and insert in its place --be--.

Column 14, Line 29, after "whether", delete --it--.

Column 15, Line 20, delete "even", and insert in its place --event--.

UNITED STATES PATENT AND TRADEMARK OFFICE
CERTIFICATE OF CORRECTION

PATENT NO. : 5,243,980
DATED : September 14, 1993
INVENTOR(S) : Rahul Mehra

It is certified that error appears in the above-indentified patent and that said Letters Patent is hereby corrected as shown below:

Column 20, Line 62, before "ventricles" please add --atria of said heart leading to depolarizations of the--.

Signed and Sealed this

Fourth Day of October, 1994

Attest:

BRUCE LEHMAN

Attesting Officer

Commissioner of Patents and Trademarks